(12) United States Patent
Onuma et al.

(10) Patent No.: US 11,426,190 B2
(45) Date of Patent: *Aug. 30, 2022

(54) ULTRASONIC SURGICAL SYSTEM AND METHOD OF OPERATING ULTRASONIC SURGICAL SYSTEM

(71) Applicant: OLYMPUS CORPORATION, Hachioji (JP)

(72) Inventors: Chie Onuma, Tama (JP); Yasuo Tanigami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 474 days.

This patent is subject to a terminal disclaimer.

(21) Appl. No.: 16/436,013

(22) Filed: Jun. 10, 2019

(65) Prior Publication Data

US 2019/0290317 A1 Sep. 26, 2019

Related U.S. Application Data

(63) Continuation of application No. PCT/JP2016/086740, filed on Dec. 9, 2016.

(51) Int. Cl.
*A61B 17/32* (2006.01)
*A61B 18/12* (2006.01)
(Continued)

(52) U.S. Cl.
CPC ...... *A61B 17/320068* (2013.01); *A61B 17/00* (2013.01); *A61B 18/1206* (2013.01);
(Continued)

(58) Field of Classification Search
CPC .......... A61B 17/320068; A61B 2017/320073; A61B 2017/003; A61B 2017/00106; A61B 2017/00119; A61B 2090/065
See application file for complete search history.

(56) References Cited

U.S. PATENT DOCUMENTS 10,188,418 B2 * 1/2019 Onuma .......... A61B 17/320068
2015/0094723 A1 * 4/2015 Darian .................. A61B 17/16
606/79

FOREIGN PATENT DOCUMENTS

JP H07-23974 A 1/1995
JP H11-70118 A 3/1999
(Continued)

OTHER PUBLICATIONS

Jan. 31, 2017 International Search Report issued in International Patent Application No. PCT/JP2016/086740, pp. 1-5.
(Continued)

*Primary Examiner* — Wade Miles
*Assistant Examiner* — Mohammed S Adam
(74) *Attorney, Agent, or Firm* — Oliff PLC

(57) ABSTRACT

An ultrasonic surgical system includes an ultrasonic transducer, a probe, and at least one circuit. The ultrasonic transducer is designed to ultrasonically vibrate. The probe is coupled to the ultrasonic transducer and is designed to treat a living tissue by the ultrasonic vibration. The circuit performs functions including detecting a pressing force of the probe against the living tissue, calculating a value of a product of the pressing force, an amplitude of the ultrasonic vibration, and a resonance frequency of the probe, comparing the calculated value with a predetermined product value, and generating a predetermined signal based on a result of the comparison.

20 Claims, 7 Drawing Sheets

(51) Int. Cl.
*A61B 17/00* (2006.01)
*A61B 18/00* (2006.01)
*A61B 90/00* (2016.01)

(52) U.S. Cl.
CPC .............. *A61B 2017/0003* (2013.01); *A61B 2017/00017* (2013.01); *A61B 2017/00026* (2013.01); *A61B 2017/00106* (2013.01); *A61B 2017/00115* (2013.01); *A61B 2017/00119* (2013.01); *A61B 2017/00973* (2013.01); *A61B 2017/320073* (2017.08); *A61B 2017/320075* (2017.08); *A61B 2018/00994* (2013.01); *A61B 2090/065* (2016.02)

(56) References Cited

FOREIGN PATENT DOCUMENTS

| | | |
|---|---|---|
| JP | 2003-235862 A | 8/2003 |
| JP | 2016-531631 A | 10/2016 |
| WO | 2010/076869 A1 | 7/2010 |

OTHER PUBLICATIONS

Jul. 5, 2021 Office Action issued in Chinese Patent Application No. 201680091473.4, pp. 1-13.
Jun. 11, 2019 International Preliminary Report on Patentability issued in International Application No. PCT/JP2016/086740, pp. 1-6.

\* cited by examiner

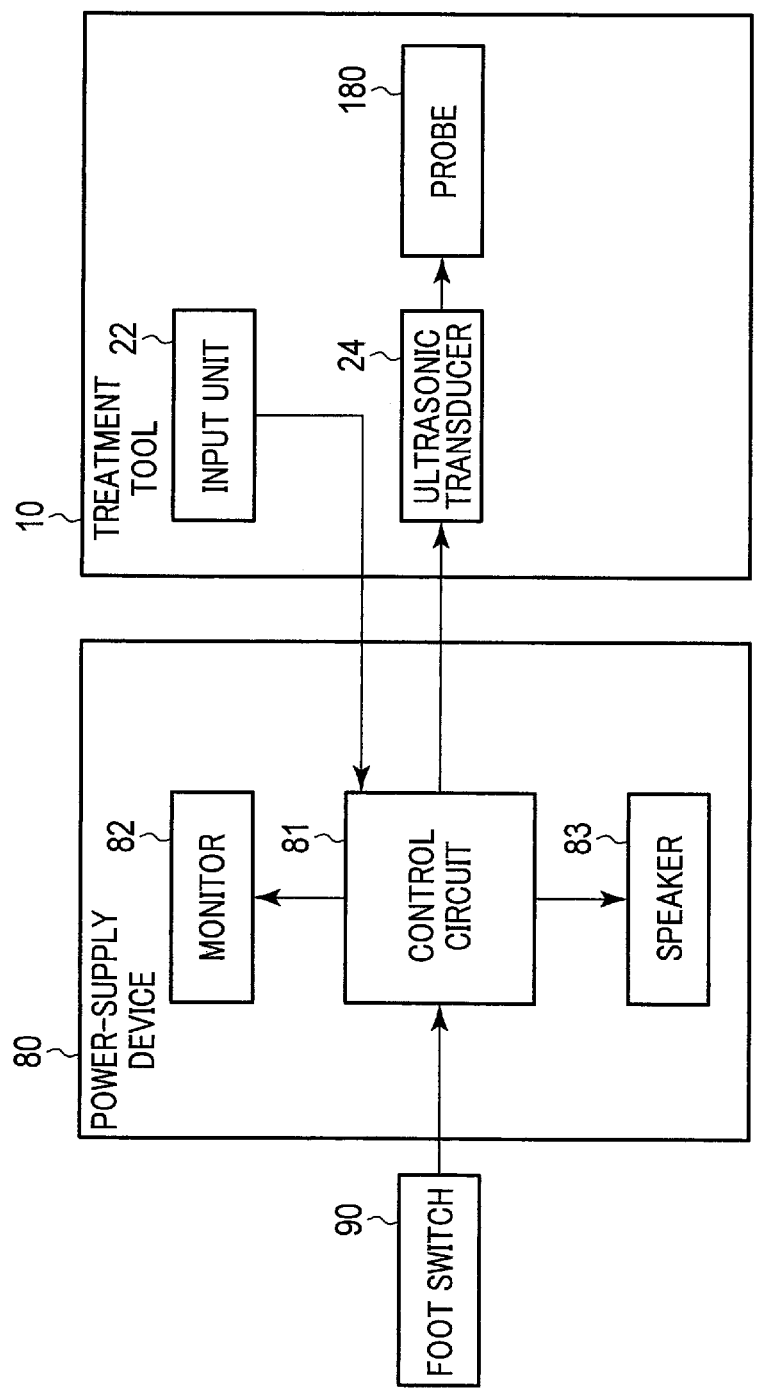
F I G. 2

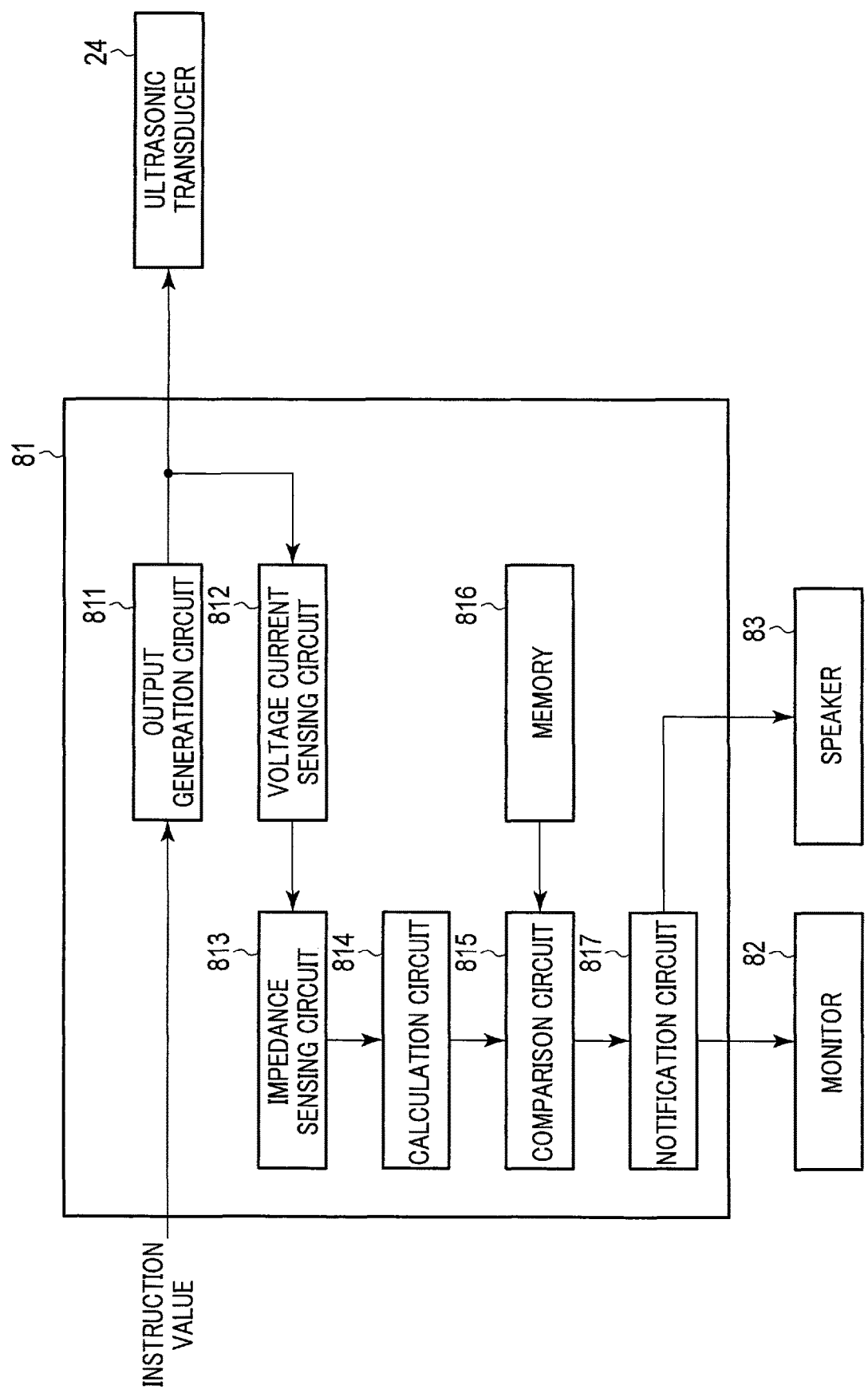
F I G. 3

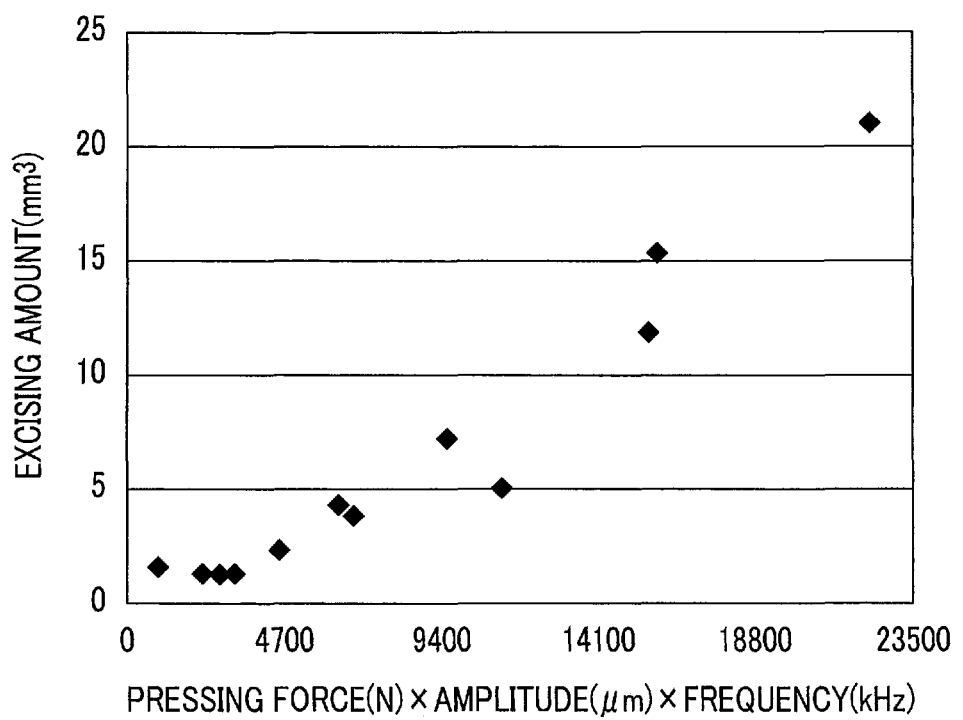
F I G. 5

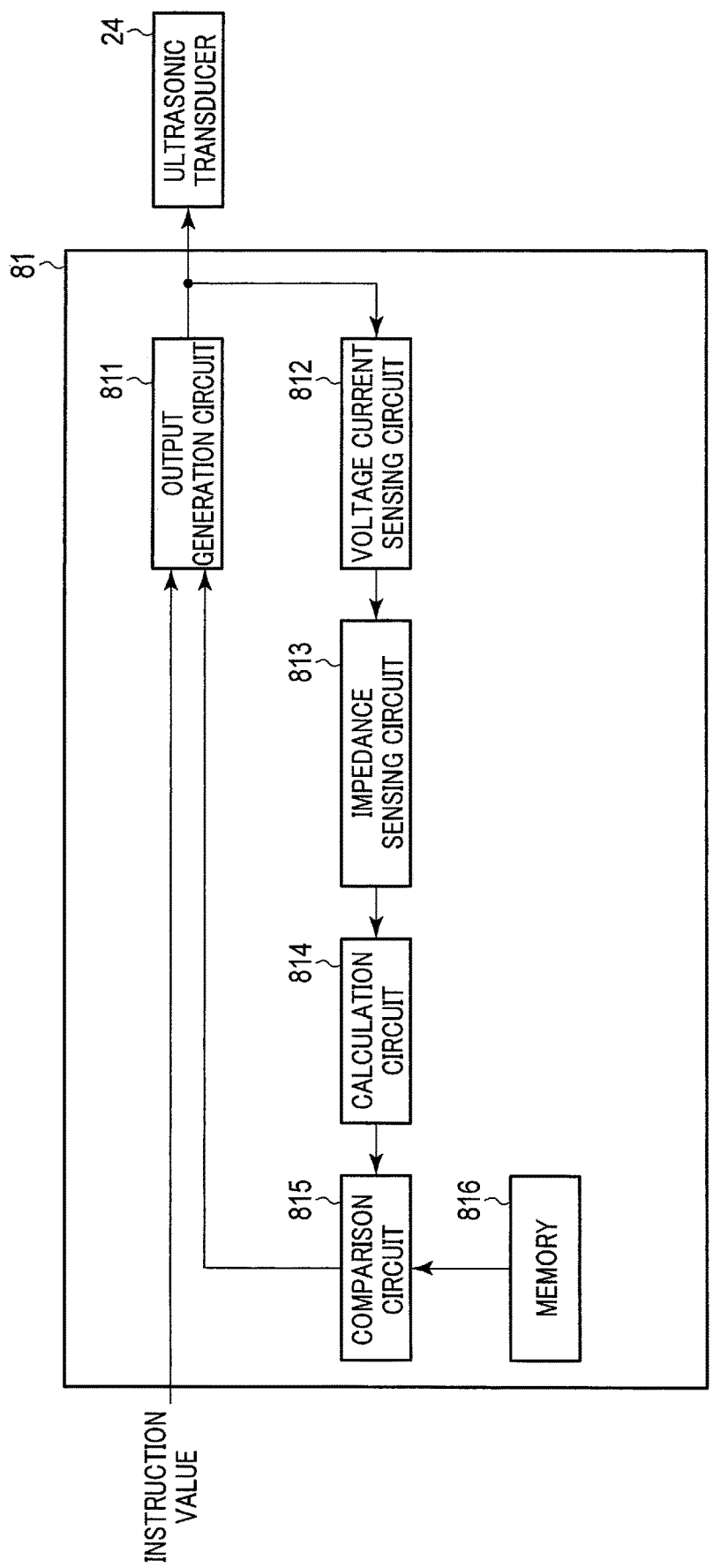
F I G. 6

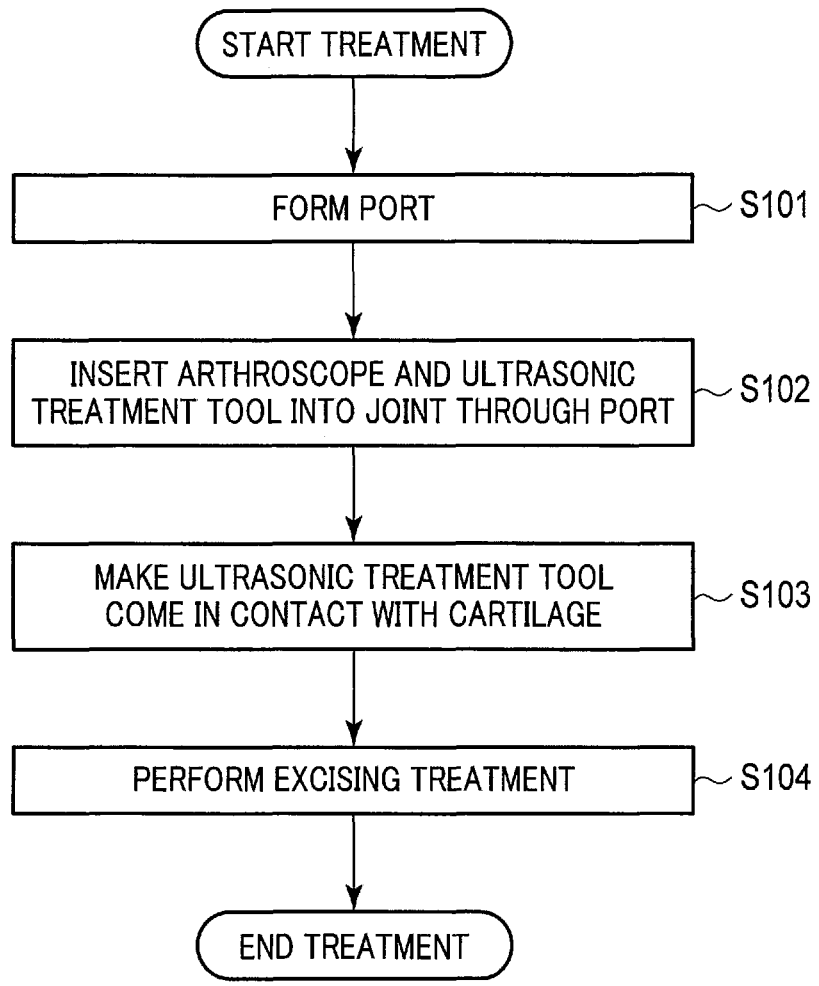
F I G. 7

US 11,426,190 B2

ULTRASONIC SURGICAL SYSTEM AND METHOD OF OPERATING ULTRASONIC SURGICAL SYSTEM

This application is a Continuation Application of PCT Application No. PCT/JP2016/086740, filed Dec. 9, 2016, the entire contents of which are incorporated herein by reference.

Exemplary embodiments relate to an ultrasonic surgical system and a method of operating the ultrasonic surgical system.

BACKGROUND

An ultrasonic surgical instrument is known as one of the treatment tools for treating a living tissue. The ultrasonic surgical instrument is configured to treat a living tissue by pressing a probe that is ultrasonically vibrating against the living tissue that is a treatment target. In order to perform treatment efficiently, it is important to perform the pressing with an appropriate pressing force. Therefore, for example, an ultrasonic surgical instrument may be configured to sense a pressing force by a spring that mechanically changes in accordance with a pressing force that is applied when a probe is made to contact a living tissue, and a detection means that detects changes in the spring, and is configured to generate ultrasonic vibration when the sensed pressing force is within a desired range.

SUMMARY

Disclosed herein is an ultrasonic surgical system comprising: an ultrasonic transducer configured to ultrasonically vibrate; a probe coupled to the ultrasonic transducer and configured to treat a living tissue by the ultrasonic vibration; and at least one circuit configured to: detect a pressing force of the probe against the living tissue; calculate a value of a product of the pressing force, an amplitude of the probe, and a resonance frequency of the probe; compare the calculated value with a predetermined product value; and generate a predetermined signal based on a result of the comparison.

The present disclosure also relates to a method of operation of an ultrasonic surgical system comprising: detecting a pressing force of an ultrasonically vibrating probe of the system against a living tissue; calculating, via a circuit of the system, a value of a product of the pressing force, an amplitude of the ultrasonic vibration of the probe, and a resonance frequency of the probe; comparing, via the circuit, the calculated value with a predetermined product value; and generating a predetermined signal based on a result of the comparison.

Advantages of the embodiments will be set forth in the description which follows, and in part will be apparent from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 2 is a block diagram showing a main configuration of an ultrasonic surgical system in an exemplary embodiment;

FIG. 3 is a block diagram showing a configuration of a control circuit in an exemplary embodiment;

FIG. 5 is a graph showing an experimental result of measuring changes in an excising amount when changing a pressing force or an amplitude with respect to a cartilage;

FIG. 6 is a block diagram showing a configuration of a control circuit in an exemplary embodiment; and FIG. 7 is a flowchart showing a flow of a treatment using the ultrasonic surgical system.

DETAILED DESCRIPTION

Hereinafter, embodiments of the present disclosure will be explained with reference to the drawings.

Figure 1:
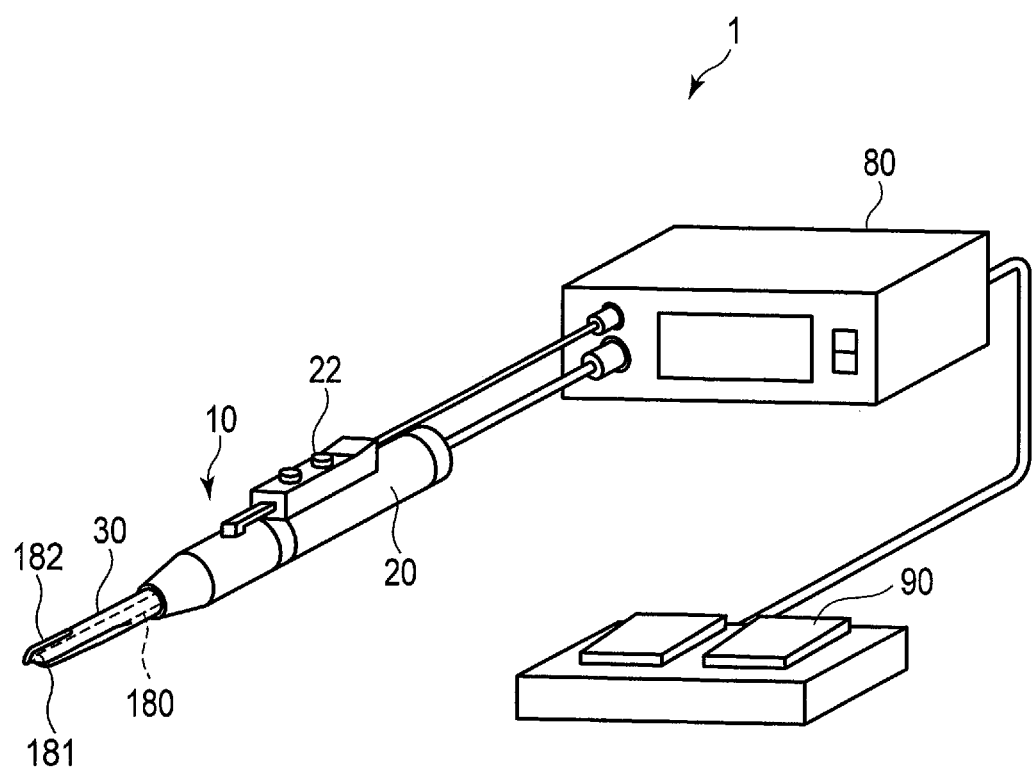
FIG. 1 shows a configuration of an ultrasonic surgical system according to each embodiment.

FIG. 1 shows a configuration of an ultrasonic surgical system 1 according to each embodiment of the present disclosure. The ultrasonic surgical system 1 comprises a treatment tool 10 for treating a living tissue by an ultrasonic wave, a power-supply device 80 for supplying a drive power to the treatment tool 10, and a foot switch 90. The ultrasonic surgical system 1 comprises a cortical bone/cancellous bone excising mode which is a mode suitable for excising hard bones such as cortical bone, and a cartilage excising mode which is a mode suitable for excising cartilage. However, the ultrasonic surgical system 1 may also be used for treatments other than excising bone.

The treatment tool 10 comprises a handpiece 20, a probe 180 protruding from the handpiece 20, and an elongated sheath 30 formed around the probe 180. In the following explanation, the treatment tool 10 on the probe 180 side will be referred to as the distal end side, and the treatment tool 10 on the handpiece 20 side will be referred to as the proximal end side of the treatment tool 10.

The handpiece 20 comprises an ultrasonic transducer therein. The ultrasonic transducer ultrasonically vibrates in accordance with the drive power from the power-supply device 80. The handpiece 20 transfers the ultrasonic vibration generated at this ultrasonic transducer to the probe 180. The probe 180 is connected to the ultrasonic transducer and vibrates in conjunction with the vibration of the ultrasonic transducer.

The distal end of the sheath 30 is formed in a semi-cylindrical shape, and a treatment unit 181 provided at a portion formed in this semi-cylindrical shape to the distal end of the probe 180 is exposed. At the distal end of the sheath 30, for example, a cold knife 182 is formed. The cold knife 182 is formed by a corrosive-resistant metal material and is used to facilitate excising a living tissue. However, the cold knife 182 does not have to be provided.

The handpiece 20 comprises an input unit 22. The input unit 22 is a part for inputting instructions for driving the ultrasonic transducer. The input unit 22 may include a plurality of switches for switching between the cortical bone/cancellous bone excising mode and the cartilage excising mode. The input unit 22 is connected to the power-supply device 80. The ultrasonic transducer inside the handpiece 20 is also connected to the power-supply device 80. The power-supply device 80 detects an input to the input unit 22 and supplies a drive power in accordance with the input to the ultrasonic transducer.

The foot switch 90 has the same function as the input unit 22 provided on the handpiece 20. In other words, likewise the input unit 22, the foot switch 90 may include a plurality of switches for switching between the cortical bone/cancellous bone excising mode and the cartilage excising mode. When detecting an input to the foot switch 90, the power-supply device 80 supplies a drive power in accordance with the input to the ultrasonic transducer. At least one of the input unit 22 or the foot switch 90 needs to be provided.

When performing a treatment, a user holds the handpiece 20 and makes the treatment unit 181 provided on the ultrasonically vibrating probe 180 come in contact with a living tissue that is a treatment target. When doing so, the user vibrates the ultrasonic transducer by operating the input unit 22 or the foot switch 90. The vibration generated at the ultrasonic transducer is transferred to the probe 180. By making the treatment unit 181 of the vibrating probe 180 come in contact with the living tissue, a treatment of excising the living tissue, etc. is performed.

FIG. 2 is a block diagram showing a main configuration of the ultrasonic surgical system 1 in the present embodiment. In FIG. 2, the explanation of configurations that are the same as those explained in FIG. 1 will be omitted by applying the same reference symbols as those in FIG. 1.

As shown in FIG. 2, the power-supply device 80 comprises a control circuit 81, a monitor 82, and a speaker 83.

The control circuit is configured as an IC that comprises, for example, an output generation circuit which generates a drive power of an ultrasonic transducer 24, and a circuit which notifies to an operator whether or not the treatment of a cartilage performed by the operator is performed appropriately. The control circuit 81 controls the drive power of the ultrasonic transducer 24 in accordance with the input from the input unit 22 or the foot switch 90. The control circuit 81 also determines whether or not the treatment of the cartilage is performed appropriately, and, in accordance with the determination result, for example, notifies whether or not the current pressing of the probe 180 is appropriate by using, for example, the monitor 82, the speaker 83, or both.

The monitor 82 is, for example, a liquid crystal display, and displays various images based on a control carried out by the control circuit 81. The speaker 83 issues various sounds based on a control carried out by the control circuit 81.

FIG. 3 is a block diagram showing an exemplary configuration of the control circuit 81 in the present embodiment. The control circuit 81 comprises an output generation circuit 811, a voltage current sensing circuit 812, an impedance sensing circuit 813, a calculation circuit 814, a comparison circuit 815, a memory 816, and a notification circuit 817.

The output generation circuit 811 comprises a power supply generation circuit, such as a regulator. When the input unit 22 or the foot switch 90 is operated, the output generation circuit 811 generates a drive power of the ultrasonic transducer 24 so that the ultrasonic transducer 24 vibrates with an amplitude corresponding to an instruction value from the input unit 22 or the foot switch 90.

With regard to the amplitude in the cartilage excising mode and the amplitude in the cortical bone/cancellous bone excising mode, the amplitude in the cartilage excising mode is set higher. This is because, in the cartilage excising mode, the excising is mainly performed by frictional heat caused by the ultrasonic vibration. Here, if a heat quantity Q [J] when an object of mass m [kg] slides s [m] on a rough horizontal surface of a dynamic friction coefficient μ', and a gravity acceleration of g(m/s$^2$) is assumed, the following (Formula 1) may be given.

$$Q = \mu' mgs \quad \text{(Formula 1)}$$

In (Formula 1), when assuming that a pressing force is a perpendicular component of a force against a rough surface, the magnitude of a pressing force (N) of the probe 180 may be considered as corresponding to mg of the above formula. Furthermore, s corresponds to an amplitude of a longitudinal vibration of an ultrasonic probe. Therefore, if the pressing force is constant, the excising amount of the cartilage would increase as the amplitude of the probe 180 increases. Furthermore, (Formula 1) is a heat quantity for one vibration. The heat quantity Q also increases proportionally with the frequency of the ultrasonic probe. Therefore, in the cartilage excising mode, in order to improve excising efficiency, at least one of the amplitude of the ultrasonic vibration and the frequency (resonance frequency) of the ultrasonic probe is set to be as large as possible. On the other hand, in the cortical bone/cancellous bone excising mode, excising is performed by an impact caused by the ultrasonic vibration rather than the frictional heat caused by the ultrasonic vibration. In the cortical bone/cancellous bone excising mode, the frictional heat caused by the ultrasonic vibration does not contribute much to the excising. Therefore, the amplitude of the ultrasonic vibration and the resonance frequency of the ultrasonic probe in the cortical bone/cancellous bone excising mode may be set smaller than the amplitude and the resonance frequency of the ultrasonic probe in the cartilage excising mode. Here, the pressing force is assumed as a vertical component of a force against a rough surface; however, for example, it is also possible to consider the pressing force as a force in an angled state with respect to verticality.

The voltage current sensing circuit 812 senses each of the output voltage and the output current of the output generation circuit 811.

The impedance sensing circuit 813 calculates the impedance of the ultrasonic transducer 24 from the comparison between the output voltage and the output current sensed at the voltage current sensing circuit 812. The impedance of the ultrasonic transducer 24 may change in accordance with the pressing force of the probe 180 against the living tissue. Accordingly, the impedance sensing circuit 813 functions as a sensing circuit that indirectly senses the pressing force of the probe 180 by detecting the impedance of the ultrasonic transducer 24. The impedance of the ultrasonic transducer 24 may also change by the type of living tissue against which the ultrasonic transducer 24 is pressed, and by temperature. Accordingly, when calculating the pressing force from the impedance, it is preferable to revise the value of the impedance in accordance with the type of the living tissue, and by temperature. Furthermore, the impact on the impedance caused by the change in the pressing force is smaller than the impact caused by the type of the living tissue and the change in temperature. Therefore, when calculating the pressing force from the impedance, the impact caused by the type of the living tissue and the temperature may be ignored.

The calculation circuit 814 converts the value of the impedance sensed by the impedance sensing circuit 813 into a value of the pressing force. The calculation circuit 814 calculates the product of the converted value of the pressing force, the current amplitude of the probe, and the current resonance frequency of the probe.

The comparison circuit 815 compares the product value calculated by the calculation circuit 814 and a product value stored in the memory 816. The comparison circuit 815 instructs the notification circuit 817 to issue a notification in accordance with the comparison result.

The range of the product value stored in the memory 816 is decided by the balance between the excising amount and heat invasion. Furthermore, a different range of product values is used between the cortical bone/cancellous bone excising mode and the cartilage excising mode. Details will be explained later on. The memory 816 stores a table for converting the value of the impedance sensed at the impedance sensing circuit 813 into the value of the pressing force. For example, this table is obtained by actual measurement of the change in impedance when the pressing force of the probe 180 is changed variously in a state where the amplitude of the probe 180 is a constant value.

In accordance with an instruction from the comparison circuit 815, the notification circuit 817 generates a signal for notifying the operator using the monitor 82 and the speaker 83. This notifies whether or not the current treatment carried out by the operator is appropriate. The notification may be a notice to prompt the user to change the pressing force, a notice to prompt the user to change the amplitude of the probe, or a notice to prompt the user to change the resonance frequency of the probe by replacing the ultrasonic transducer, etc.

Figure 4:
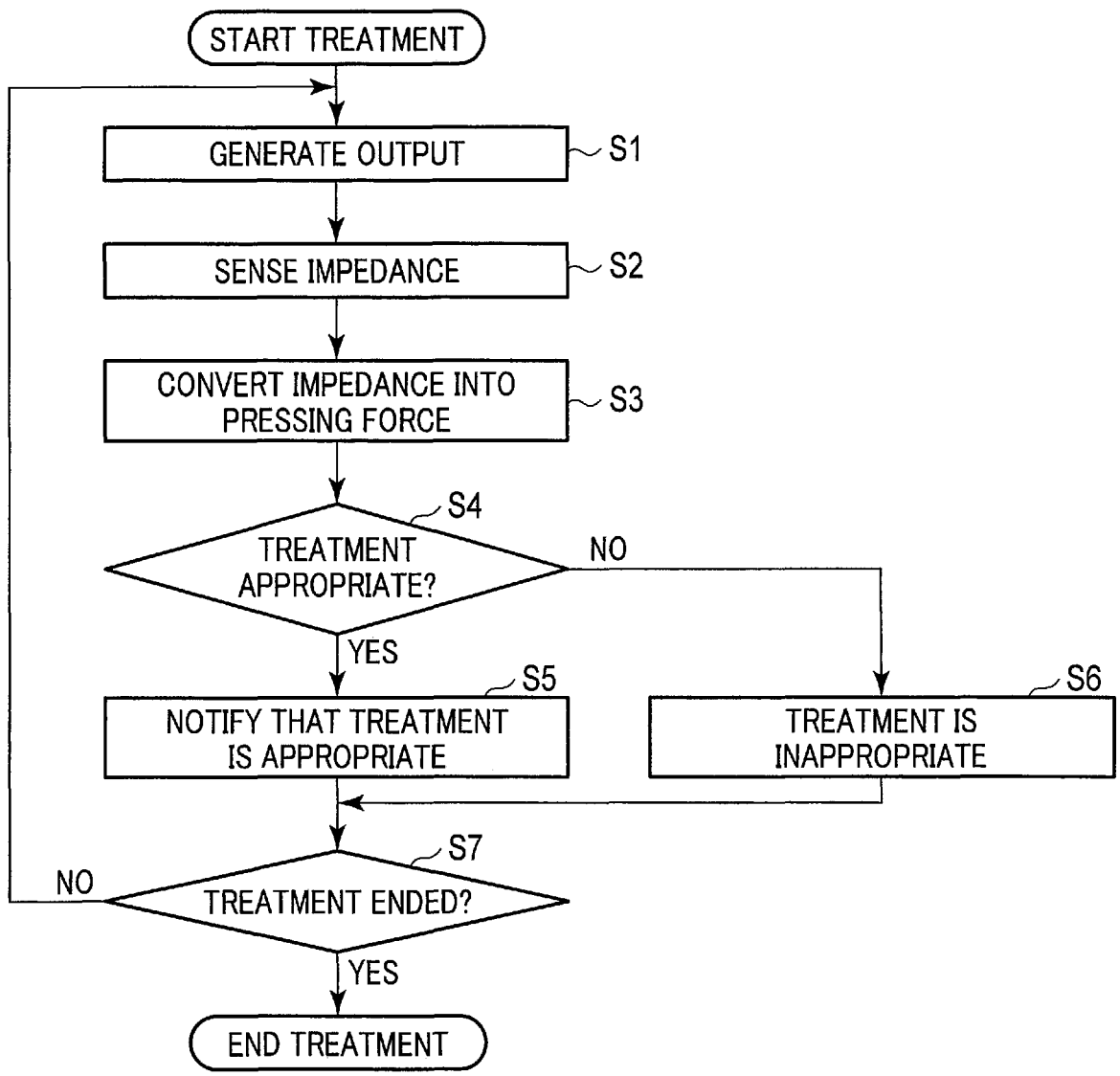
FIG. 4 is a flow chart showing an operation of the ultrasonic surgical system.

An operation of the ultrasonic surgical system 1 according to the present embodiment is explained below. FIG. 4 is a flow chart showing the operation of the ultrasonic surgical system 1. For example, the processing in FIG. 4 is started when the power of the ultrasonic surgical system 1 is turned on and the input unit 22 or the foot switch 90 is operated.

In step S1, the output generation circuit 811 generates the drive power for driving the ultrasonic transducer 24. When the cartilage excising mode is instructed by the input unit 22 or the foot switch 90, the output generation circuit 811 generates the drive power so as to cause the ultrasonic vibration to occur with an amplitude corresponding to an instruction value preset for the cartilage excising mode. On the other hand, when the cortical bone/cancellous bone excising mode is instructed by the input unit 22 and the foot switch 90, the output generation circuit 811 generates the drive power so as to cause the ultrasonic vibration to occur with an amplitude corresponding to an instruction value present for the cortical bone/cancellous bone excising mode. The output generation circuit 811 may be configured to feedback control the drive power. In this case, for example, the output current of the output generation circuit 811 sensed at the voltage current sensing circuit 812 is returned to the output generation circuit 811. The output generation circuit 811 controls the output voltage so that the returned output current becomes consistent with the instruction value.

In step S2, the impedance sensing circuit 813 calculates the impedance of the ultrasonic transducer 24 from the ratio of the output voltage and the output current sensed by the voltage current sensing circuit 812.

In step S3, the calculation circuit 814 converts the value of the impedance calculated at the impedance sensing circuit 813 into the value of the pressing force in accordance with the table stored in advance in the memory 816. The calculation circuit 814 then calculates the product of the current value of the pressing force obtained from the value of the impedance, the current amplitude of the probe, and the current resonance frequency of the probe.

In step S4, the comparison circuit 815 compares the product value calculated at the calculation circuit 814 and the product value stored in advance in the memory 816. The comparison circuit 815 then determines whether or not the current treatment of the cartilage carried out by the operator is appropriate based on the comparison result. For example, if the current product value exceeds the product value stored in advance in the memory 816, the current treatment of the cartilage is determined as appropriate.

The range of the pressing force is explained below. FIG. 5 is a graph showing an experimental result of measuring changes in the excising amount when the value of the product of the pressing force, the amplitude, and the resonance frequency is changed with respect to the cartilage. FIG. 5 shows an average value of the excising amount (the volume of the excised cartilage) at six points (N=6) of the cartilage of the measuring target. Although FIG. 5 shows changes in an excising amount of cartilage, the present disclosure also relates to changes in an excised amount of bone (e.g., volume of the excised cortical or cancellous bone) when the value of the product of the pressing force, amplitude, and resonance frequency are changed.

As shown in FIG. 5, in the case of the cartilage, as an overall trend, the excising amount increases as the product of the pressing force, the amplitude, and the resonance frequency increases. However, in the case of the cartilage, if the product value is equal to or less than 4700 [N µm kHz], the cartilage will not dissolve, and the excising will not progress. This is because the cartilage is excised mainly by frictional heat caused by ultrasonic vibration. Accordingly, in the present embodiment, a value of the product value 4700 [N µm kHz] is stored in the memory 816.

In this manner, the comparison circuit 815 compares the value with the current product value by the relationship shown in FIG. 5. In step S4, when the current treatment of the cartilage is determined as appropriate, the processing moves on to step S5. In step S4, when the current treatment of the cartilage is determined as inappropriate, the processing moves on to step S6.

In step S5, the comparison circuit 815 notifies the notification circuit 817 that the current cartilage treatment is appropriate. Having received this notice, the notification circuit 817 notifies the operator that the current cartilage treatment conducted by the operator is appropriate by using the monitor 82 and the speaker 83. Subsequently, the processing moves on to step S7. The notification is performed by, for example, displaying message such as "appropriate condition" on the monitor 82, issuing a sound from the speaker 83, or using both of them.

In step S6, the comparison circuit 815 notifies the notification circuit 817 that the current cartilage treatment is inappropriate. Having received this notice, the notification circuit 817 notifies the operator by using the monitor 82 and the speaker 83. Subsequently, the processing moves on to step S7. The notification is performed by, for example, displaying message such as "Please press more strongly on the probe, increase the amplitude of the probe, or replace the ultrasonic transducer" on the monitor 82, issuing a sound from the speaker 83, or using both of them.

In step S7, the output generation circuit 811 determines whether or not to end the processing. For example, in the case where the power of the ultrasonic surgical system 1 is turned off, or in the case where the operation of the input unit 22 or the foot switch 90 is released, the processing is determined to be ended. In step S7, in the case where the processing is determined to be ended, the processing of FIG. 4 is ended. In step S7, in the case where it is determined to not end the processing, the processing returns to step S1.

As explained above, according to the present embodiment, the product of the pressing force of the probe 180 against the living tissue by the operator, the amplitude of the probe, and the resonance frequency of the probe is compared to the predetermined product value, and it is notified whether or not the current cartilage treatment by the operator is appropriate in accordance with the comparison result thereof. In this manner, the operator is capable of performing an appropriate cartilage treatment.

The processing of each step in FIG. 4 is performed by using a "circuit"; however, this may also be performed by a software.

Another exemplary embodiment of the present disclosure is explained below. The above embodiment compares the product of the current pressing force, the amplitude of the probe, and the resonance frequency of the probe with the predetermined product value, and notifies the operator in accordance with the comparison result thereof. In this embodiment the product of the current pressing force, the amplitude of the probe, and the resonance frequency of the probe is compared with the predetermined product value, and feedback control of the amplitude of the ultrasonic transducer 24 is performed in accordance with the comparison result thereof.

FIG. 6 is a block diagram showing an exemplary configuration of the control circuit 81 in the present embodiment. The control circuit 81 comprises the output generation circuit 811, the voltage current sensing circuit 812, the impedance sensing circuit 813, the calculation circuit 814, the comparison circuit 815, and the memory 816. The control circuit 81 in the present embodiment is configured to return an output of the comparison circuit 815 to the output generation circuit 811.

Similar to the output generation circuit 811 in the above embodiment, the output generation circuit 811 in the present embodiment controls the drive power so as to generate ultrasonic vibration in different amplitudes between the cortical bone/cancellous bone excising mode and the cartilage excising mode. When in the cartilage excising mode, for example, the output generation circuit 811 in the present embodiment controls increasing or decreasing the amplitude in accordance with the difference between the current product value and the product value stored in advance in the memory 816. For example, the output generation circuit 811 controls increasing or decreasing the amplitude so that the current product value becomes 4700 [N μm kHz].

As explained above, according to the present embodiment, feedback control of the amplitude is performed in accordance with the difference between the current product value and the product value stored in advance in the memory 816. Therefore, for example, the operator is able to perform treatment without changing the pressing force.

In the aforementioned example, an example of increasing or decreasing the amplitude is explained. In contrast, it may also be that the resonance frequency is changed in accordance with the difference between the current product value and the product value stored in advance in the memory 816. For example, by providing ultrasonic transducers of a plurality of different resonance frequencies in different treatment tools, the resonance frequency of the probe can be changed by switching this ultrasonic transducer.

The present disclosure also relates to a treatment method using an ultrasonic surgical system. FIG. 7 is a flow chart showing a flow of the treatment using the ultrasonic surgical system 1. FIG. 7 shows an excising treatment of a degenerating cartilage in a knee joint. The flowchart in FIG. 7 is not limited to a knee joint, and may also be applied to the treatment of other joints such as a shoulder joint.

In step S101, a doctor uses a trocar to form a port that enables a treatment tool and an arthroscope to be inserted to a position of a living tissue (here, a degenerating cartilage in a knee joint) of a treatment target.

In step S102, the doctor inserts the arthroscope and the treatment tool 10 of the ultrasonic surgical system 1 into the knee joint through the port for the arthroscope.

In step S103, while observing an image inside the knee joint displayed on a monitor through the arthroscope, the doctor makes the treatment unit 181 of the ultrasonic surgical system 1 come in contact with the degenerating cartilage which is the treatment target.

In step S104, for example, the doctor operates the input unit 22 to set the ultrasonic surgical system 1 to a cartilage dissolution mode, and, while pressing the treatment tool against the degenerating cartilage, performs excising by confirming the pressing state of the treatment tool. Here, in the case where the pressing performed by the doctor is weak, or in the case where the amplitude of the probe is small, etc., for example, a message such as "Please press more strongly on the probe, increase the amplitude of the probe, or replace the ultrasonic transducer" will be displayed on the monitor 82. Therefore, without stopping, the doctor may continue with the treatment by pressing stronger, etc. while observing the monitor 82. As a result, when an appropriate treatment is performed, for example, a message such as "appropriate condition" will be displayed. Therefore, the doctor may perform treatment while maintaining the current pressing state by observing the monitor 82.

As explained above, according to the present embodiment, since the doctor is able to intuitively ascertain whether or not the current treatment is appropriate by a sound or a display on a monitor, an efficient and safe surgery with less heat invasion may be performed without stopping.

In the case of using the system described in the present embodiment, the doctor is able to proceed with the surgery without having to care about the pressing force, etc.

The disclosed systems and methods have been explained based on the above embodiments; however, the present disclosure is in no way limited to the aforementioned embodiments. Needless to say, the present disclosure can be modified in various manners, without departing from the spirit and scope of the disclosure. For example, in each of the aforementioned embodiments, the pressing force is sensed based on the impedance of the ultrasonic transducer. However, the pressing force may also be sensed from other than the impedance of the ultrasonic transducer. For example, the pressing force may be sensed by a sensor that directly senses the force of a distortion gauge, etc. The pressing force may also be sensed from a change in the resonance frequency of the probe. The pressing force may also be sensed from a temperature.

Furthermore, a technique of identifying the state of a living tissue from an impedance of an ultrasonic transducer is also known. This technique may also be applied to each of the aforementioned embodiments. In this case, a product value is selected in accordance with the identified living tissue.

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic surgical system comprising:
   an ultrasonic transducer configured to ultrasonically vibrate;
   a probe coupled to the ultrasonic transducer and configured to treat a living tissue by the ultrasonic vibration; and
   a circuit configured to:
      detect a pressing force of the probe against the living tissue;
      calculate a value of a product of the pressing force, an amplitude of the ultrasonic vibration, and a resonance frequency of the probe;
      compare the calculated value of the product of the pressing force, the amplitude of the ultrasonic vibration, and the resonance frequency of the probe with a predetermined product value; and
      generate a predetermined signal based on a result of the comparison.

2. The ultrasonic surgical system according to claim 1, wherein the predetermined product value is 4700 (N·µm·kHz).

3. The ultrasonic surgical system according to claim 1, wherein the predetermined signal is a notification signal for notifying an operator when the calculated value is less than the predetermined product value.

4. The ultrasonic surgical system according to claim 3, wherein the notification signal is output by at least one of a sound or a display.

5. The ultrasonic surgical system according to claim 1, wherein the predetermined signal is a control signal for controlling the ultrasonic transducer to change the calculated value to the predetermined product value.

6. The ultrasonic surgical system according to claim 5, wherein the control signal is a signal to increase or decrease the amplitude of the ultrasonic vibration based on a difference between the calculated value and the predetermined product value.

7. The ultrasonic surgical system according to claim 5, wherein the control signal is a signal to change the resonance frequency of the probe based on a difference between the calculated value and the predetermined product value.

8. The ultrasonic surgical system according to claim 1, wherein the circuit is configured to detect the pressing force based on an impedance of the ultrasonic transducer.

9. The ultrasonic surgical system according to claim 8, wherein the circuit is configured to calculate the impedance from a ratio of an output voltage and an output current.

10. The ultrasonic surgical system according to claim 1, wherein the system is configured to switch between a bone excising mode and a cartilage excising mode.

11. The ultrasonic surgical system according to claim 1, further comprising a memory configured to store the predetermined product value.

12. A method of operation of an ultrasonic surgical system comprising:
    determining a pressing force of an ultrasonically vibrating probe comprised by the ultrasonic surgical system against a living tissue;
    calculating, via a circuit comprised by the ultrasonic surgical system, a value of a product of the pressing force, an amplitude of an ultrasonic vibration of the probe, and a resonance frequency of the probe;
    comparing, via the circuit, the calculated value of the product of the pressing force, the amplitude of the ultrasonic vibration, and the resonance frequency of the probe with a predetermined product value; and
    generating, via the circuit, a predetermined signal based on a result of the comparison.

13. The method according to claim 12, wherein the predetermined product value is 4700 (N·µm·kHz).

14. The method according to claim 12, wherein the predetermined signal is a notification signal for notifying an operator when the calculated value is less than the predetermined product value.

15. The method according to claim 14, wherein the notification signal is output via at least one of a sound or a display.

16. The method according to claim 12, wherein the predetermined signal is a control signal for controlling an ultrasonic transducer of the ultrasonic surgical system to change the calculated value to the predetermined product value.

17. The method according to claim 16, wherein the control signal is a signal to increase or decrease the amplitude of the ultrasonic vibration based on a difference between the calculated value and the predetermined product value.

18. The method according to claim 16, wherein the control signal is a signal to change the resonance frequency of the probe based on a difference between the calculated value and the predetermined product value.

19. The method according to claim 16, wherein the pressing force is detected based on an impedance of the ultrasonic transducer.

20. The method according to claim 12, further comprising adjusting the amplitude of the ultrasonic vibration to change the calculated value to the predetermined product value when the calculated value is different from the predetermined product value.

* * * * *